United States Patent [19]

Tanabe

[11] Patent Number: 5,704,875
[45] Date of Patent: Jan. 6, 1998

[54] DATA ACQUISITION DEVICE

[75] Inventor: Kazuhisa Tanabe, Kyoto, Japan

[73] Assignee: Omron Corporation, Kyoto, Japan

[21] Appl. No.: 504,662

[22] Filed: Jul. 20, 1995

[30] Foreign Application Priority Data

Jul. 21, 1994 [JP] Japan .................................. 6-169118

[51] Int. Cl.[6] ................................................ A63B 21/00
[52] U.S. Cl. ...................... 482/4; 482/1; 482/3; 482/901
[58] Field of Search ........................... 482/1, 3, 4, 8, 482/9, 901, 902

[56] References Cited

U.S. PATENT DOCUMENTS 5,230,673  7/1993  Maeyama et al. ................... 482/57 X
5,318,487  6/1994  Golen et al. ........................ 482/5

Primary Examiner—Jerome Donnolly
Assistant Examiner—Glenn E. Richman
Attorney, Agent, or Firm—Morrison & Foerster LLP

[57] ABSTRACT

A data acquisition device includes a receiver operable to receive a stream of data, a first input device operable to supply an identifier to identify data from the stream of data received by the receiver, a second input device operable to produce a signal indicative that data from the stream of data received by the receiver is valid, and storage operable to store the identifier supplied by the first input device in combination with data from the stream of data received by the receiver. The data acquisition device also includes a controller operable to operate the device in a monitor mode in which data from the stream of data received by the receiver is monitored and an actual measurement mode in which data from the stream of data received by the receiver is stored in the storage along with the identifier supplied by the first input device. The controller switches operation of the device from the monitor mode to the actual measurement mode when the signal from the second input device indicates that the data is valid.

10 Claims, 8 Drawing Sheets

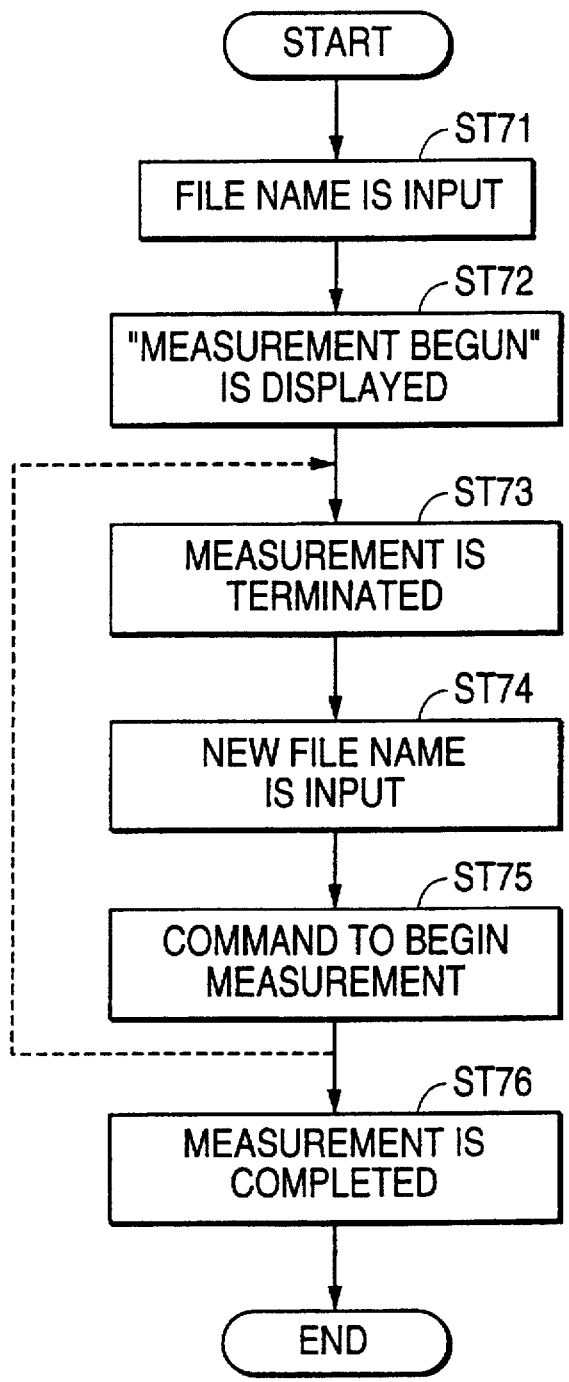

DATA ACQUISITION DEVICE

BACKGROUND OF THE INVENTION

The invention is directed generally to a device for acquiring data representing measurements obtained by a sensor, and in particular to a device for acquiring data representing measurements obtained by a sensor that detects physiological data while a person is exercising.

An ergometer is one existing device used to increase physical strength or to combat insufficient exercise. When a person trains with an ergometer, a sensor (for example, a probe consisting of a luminous element and a photodetective element) is used to detect changes in the body's oxygen level and blood volume, physical ability, condition during exercise, fatigue, and so on. Oxygen change in tissue is measured non-invasively, and from this measurement the various physical data mentioned above are obtained and output on a display.

When one wishes to measure physical variables during exercise, it is desirable to begin the measurement when the person is in a stable state. However, with existing devices to monitor exercise such as the ergometer, the person himself must guess when his state is stable and indicate that measurement should commence at that time. When measurement has begun and the data are displayed, it sometimes becomes apparent from the trend of the measurement data that the person's state is not, in fact, yet stable. When this occurs, the person must allow the measurement process to continue until his state becomes stable, at which time he must interrupt the process and direct it to restart for actual data collection. That is, at first, the person inputs a file name to store his data and starts the measurement operation. If he then learns that his state is not stable, he stops the measurement and commands whether he wishes to input a new file name, or erase or overwrite the measurement data stored under the old file name. He then starts the new measurement operation again. In other words, he has to repeat such a measurement operations many times until his physical state goes into stable condition.

Another problem with existing exercise monitors is that, although their performance can be affected by how well the sensor is attached to the person or by stray light, one cannot estimate the influence of these factors without actually beginning the measurement. If it turns out that the measurement is affected by spurious factors, it must be restarted.

SUMMARY OF THE INVENTION

The invention disclosed here was developed in view of the problems of existing exercise monitors discussed above. An object of the invention is to provide a device which would be able to verify the person's state in a simple fashion before beginning to store the actual measurement data.

The data acquisition device described in the first embodiment acquires data representing measurements obtained by a sensor which detects physiological data while a person is exercising. Its distinguishing features are that it has a monitor mode, which does not entail storage of the measurement data; a measurement mode, which does entail storage of the measurement data; and a controller that switches the device from the monitor mode to the measurement mode.

The data acquisition device described in the second embodiment is distinguished by fact that it has a concurrent monitor/measurement mode, in which a temporary file is created for measurement data; an actual measurement mode, which entails storage of the measurement data; a controller that switches the device from the monitor mode to the measurement mode; and a device that allows an operator to select, when the concurrent monitor/measurement mode is ending, whether the aforesaid measurement data file which was stored temporarily should be saved or deleted.

The data acquisition device in the first embodiment has a monitor mode which allows the person who is to be monitored to easily ascertain, prior to actual measuring the data, whether his state is stable. In monitor mode, virtually the same operations are performed as in measurement mode (data display, graph display, and so on), but the measurement data are not stored in a file. When monitor mode is chosen, the measurement data are displayed as numerical values or in the form of a graph. By observing the trend of their variation, the person can easily determine whether his state is stable. If, in the course of monitoring, the mode is switched from the monitor mode to the measurement mode, the measurement data will be stored from that point on. Subsequent workings will be identical to those of existing exercise monitor devices. Because the user can command with the switching means that data storage should begin only when he has determined that his state is stable, there is no need, as in prior art devices, to redo the measurements.

The data acquisition device described in the second embodiment operates similarly to the device described in the first embodiment. It differs only in that the data acquired in the concurrent monitor/measurement mode are stored in a temporary file. If the switching means is used to switch the mode from the concurrent monitor/measurement mode to the measurement mode, the measurement data will be stored from that point on. If the user does not indicate that data storage should begin, he may, after measurement has been completed, whether the measurement data file which was stored temporarily should be saved or deleted.

The user is provided with the ability to save or delete the temporarily stored data for the following reason: Because the operation of monitor mode is similar to that of measurement mode, the user may forget to command during monitor measurement that data storage should begin. In other words, it may happen that the user performs the exercise which he intends for measurement without ever commanding that data storage should begin. If the device is in concurrent monitor/ measurement mode when this happens, the measurement data will have been stored temporarily in a file. Even though the concurrent monitor/measurement mode has been completed without his ever commanding that the data should be recorded, the user can, by indicating that the file should be saved, create an actual data file from the temporary file. This function in effect makes it difficult for the user to forget to record the measurement data.

The measurement data referred to in regard to the invention include quantities which do not vary during the measurement process, such as the time that measurement began, the sampling interval used for measurement, the static parameters of the data acquisition device, and so on, as well as quantities which vary with each sample, such as time data indicating when the sampling was done, the values for the intensity of light transmitted with respect to various wavelengths and the offset value for the dark periods, measurement values for physical quantities such as temperature which affect the quantities which one ultimately wishes to obtain, measurement parameters which vary dynamically, for example, the gain of the data acquisition device, marking data which indicate the timing of changes in the intensity or style of the exercise, values for tissue oxygen and blood volume change calculated from various of the values stated above, or a selection of the values mentioned above. With respect to data indicating the times when the data were sampled, the time that measurement was begun and the sampling interval are stored. It is thus possible to reduce the size of data file which must be stored if we compute sampling times by adding sampling intervals to the time measurement was begun.

The invention features a data acquisition device having a receiver that receives a stream of data, a first input device that supplies an identifier to identify data from the stream of data, a second input device that produces a signal indicative of whether the data is valid, storage such as an IC card for storing the identifier supplied by the first input device in combination with the data, and a controller. The controller operates the device in a monitor mode in which data is monitored and a measurement mode in which data is stored in the storage along with the identifier, and switches operation of the device from the monitor mode to the measurement mode when the signal produced by the second input device indicates that the data is valid.

The device may also include a display that displays measurements based on the data, and, when the device is operating in the monitor mode, may display the measurements without storing the data in the storage. The data may be produced by a sensor that detects physiological data while a person is exercising, such as a sensor associated with an ergometer.

When operating in the monitor mode, the device may temporarily store data in the storage, and may display measurements based on the data. In this case, the controller responds to a signal indicative of whether to abandon or save the temporarily-stored data by either erasing the temporarily stored data from the storage when the signal indicates that the data should be abandoned or saving the temporarily stored date when the signal indicates that the data should be saved. Typically, the controller erases or saves the temporarily stored data when the controller switches operation of the device from the monitor mode to the measurement mode.

BRIEF DESCRIPTION OF THE DRAWING

FIG. 8 is a flowchart of the operation of a prior art device.

DESCRIPTION OF THE PREFERRED EMBODIMENTS

Figure 1:
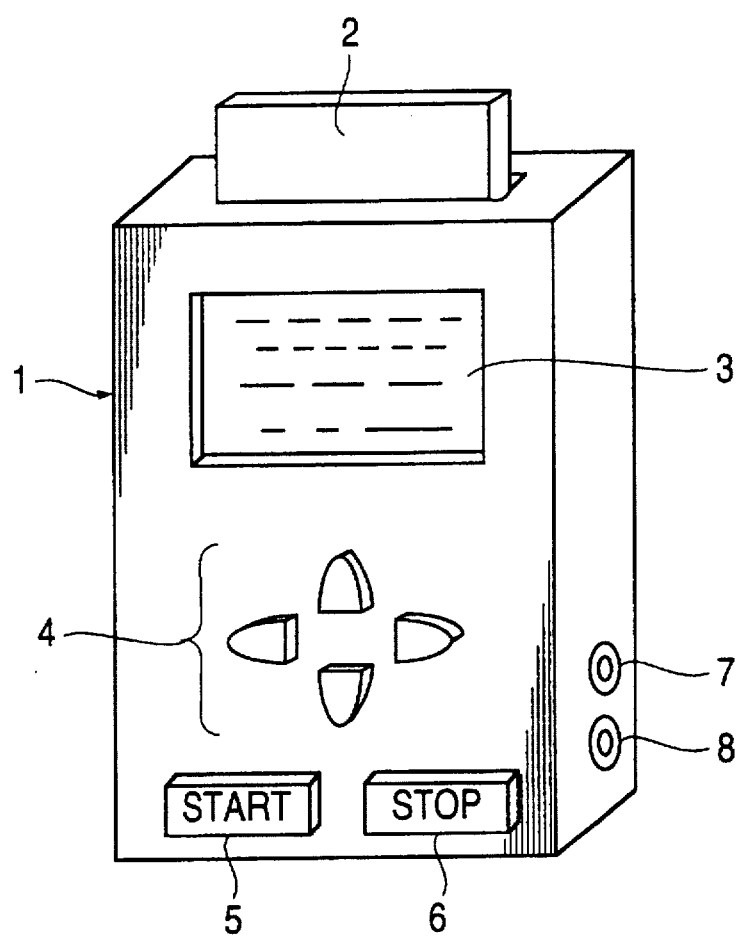
FIG. 1 is a perspective drawing of a data acquisition device.

FIG. 1 shows an external view of a data acquisition device 1, which is a compact, portable device, having the following features. A storage in the form of an IC card 2, on which an individual's measurement data are stored, can be inserted into device 1. A display 3, on the front of the device, displays the measurement data either as numerical values or in the form of a graph. Keys 4, a start button 5, and a stop button 6 are included as input devices, where keys 4 are used to move the cursor in display 3 to select operations displayed by the display, start button 5 is used to indicate when measurement should begin, and stop button 6 is used to indicate when it should cease. On the side of device 1 are a jack 7, which is used to connect the device to a host computer (the jack conforms to the RS-232C standard), and a jack 8, which is used to connect the sensor (or probe) that actually collects the physiological data during exercise and to thereby permit the device to receive data from the sensor.

Figure 2:
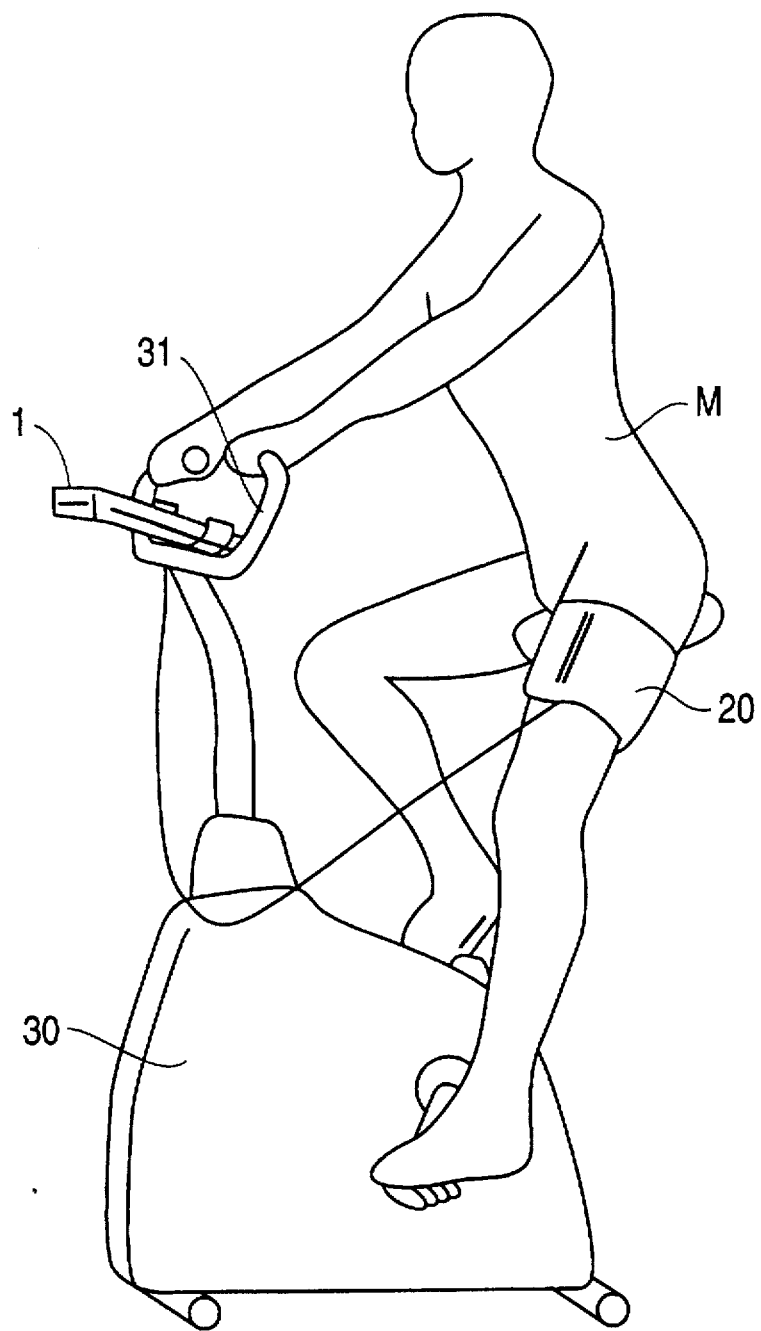
FIG. 2 is a perspective drawing of the data acquisition device of FIG. 1 in combination with an ergometer.

The data acquisition device described above is ideally suited for use with the ergometer 30 illustrated in FIG. 2. When it is so used, device 1 is installed on the handlebar 31 of ergometer 30. Sensor probe 20, which is attached to subject M's thigh, is connected to jack 8 on device 1.

Figure 3:
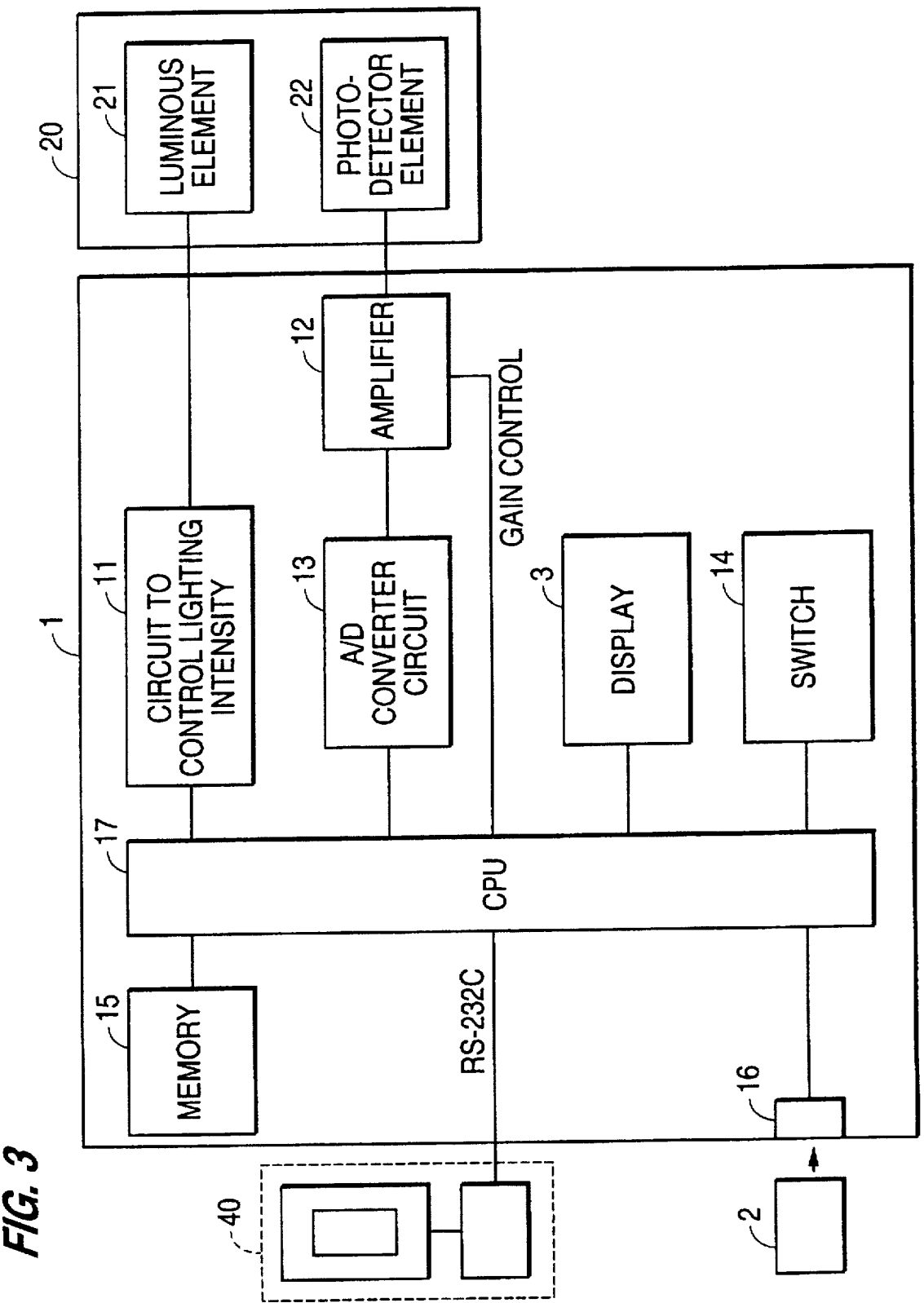
FIG. 3 is a block diagram of electronic circuitry of the device in FIG. 2.

FIG. 3 is a block diagram showing the overall configuration of the circuitry in this device. Sensor probe 20 includes luminous elements 21 (LEDs or the like), which emit, for example, two wavelengths of near-infrared light into biological tissue; and photodetectors 22 (photodiodes or the like), which detect the light reflected by the biological tissue. Thus, sensor probe 20 produces, via photodetectors 22, a stream of data that is related to the light reflected by the biological tissue. Data acquisition device 1 includes the following: circuit 11, which controls the strength of light emitted by luminous element 21; amplifier 12, which receives and amplifies the stream of data from photodetector 22; A/D converter 13, which digitizes the amplified analog signal corresponding to the stream of data; display 3, which displays the measurement data as numerical values or in the form of a graph; switching unit 14, which includes start and stop buttons 5 and 6; memory 15, which includes a ROM that stores the software needed to control the device and a RAM that stores the control and measurement data; interface 16, which connects IC card 2 to the device; and CPU 17 (i.e., a controller), which oversees the control of all of these various parts. Both or either of the RAM and ROM in memory 15 may be a flash memory, and a card-type hard disk may be substituted for IC card 2.

CPU 17 in data acquisition device 1 conforms, for example, to an RS-232C, and can, if desired, be connected to host computer 40. In this way the measurement data collected by device 1 can be sent to computer 40, and during monitor measurement, they can be displayed by the host computer as numerical values or in the form of a graph. When host computer 40 is used, the command to begin recording measurement data and the commands to be executed when monitor measurement is finished can be entered via the computer keyboard instead of via switches 14 in data acquisition device 1.

Figure 4:
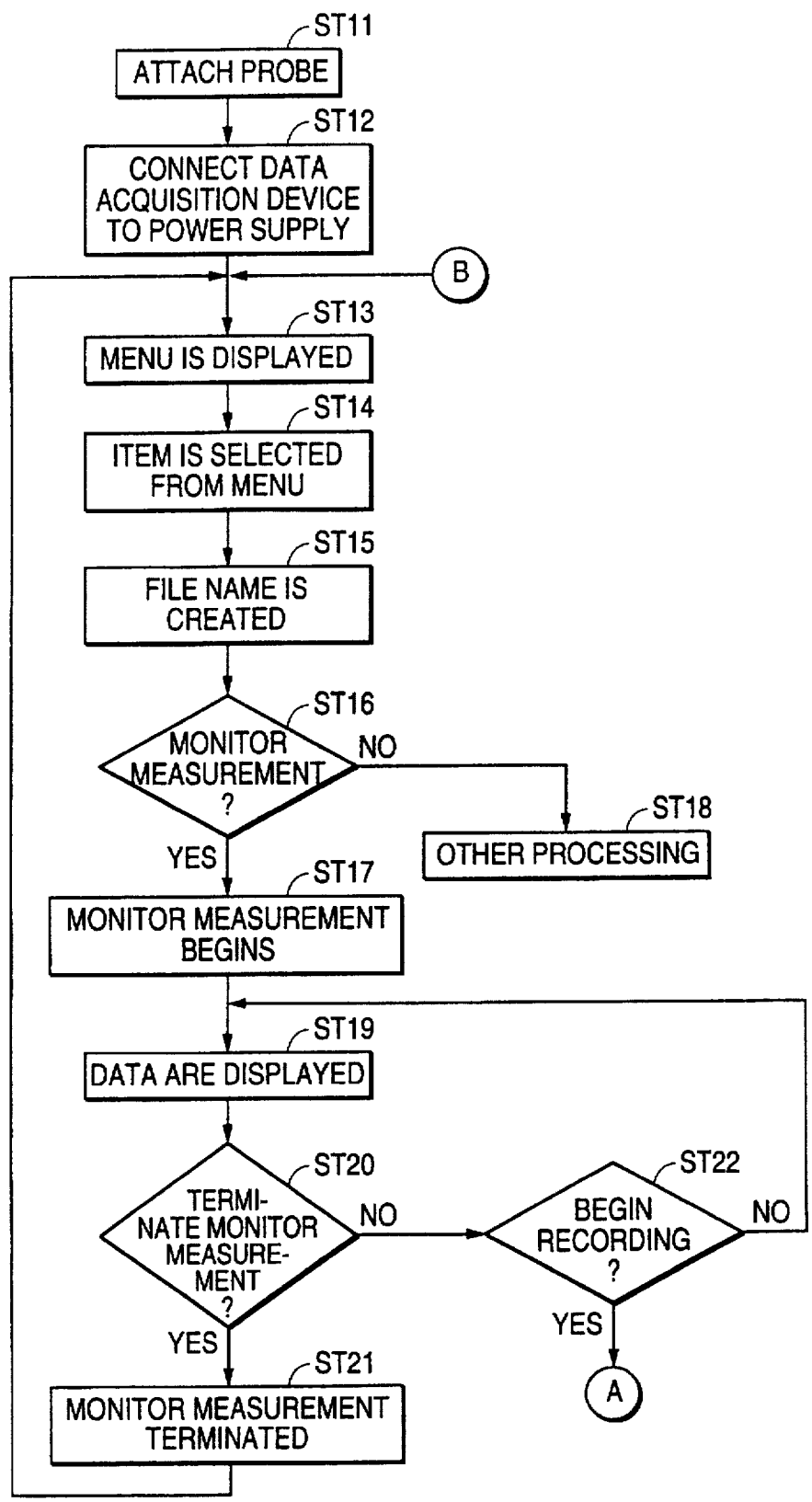
FIGS. 4 and 5 are flowcharts illustrating the operation of a first embodiment of the device of FIG. 1.
Figure 5:
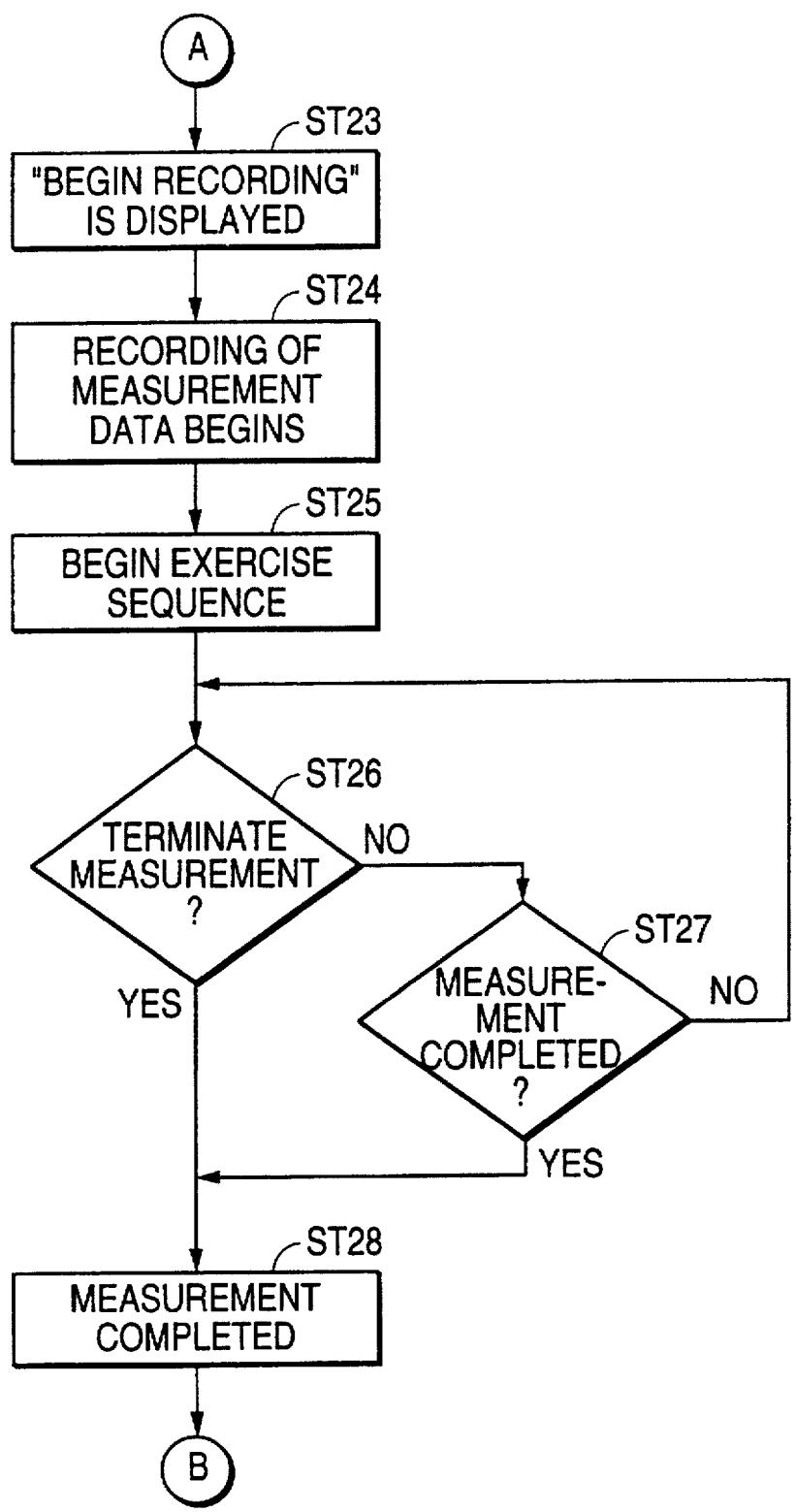

Next we shall explain how data acquisition device 1 in the first embodiment works in monitor measurement mode when it is installed on ergometer 30, with reference to the flowchart in FIGS. 4 and 5.

First, subject M attaches sensor probe 20 to the part of the body where the measurements are to be made (the thigh), and he connects the probe to jack 8 on device 1 (ST 11). When power is supplied to device 1 (ST 12), the main menu is shown on display 3 (ST 13). The main menu allows the user to select monitor or actual measurement mode, set the parameters of measurement, and select a variety of other parameters, including the operation of IC card 2 and settings for communication. In this case, since we wish to select monitor measurement (i.e., monitor measurement mode), we use keys 4 on device 1 to move the cursor on display 3 until it indicates monitor measurement (ST 14). When monitor measurement mode is selected, the user must decide whether the name of the file in which the measurement data are to be stored should be determined automatically or whether he wishes to choose a name from a selection of file names which he has reserved previously (ST 15). If device 1 is to create the file name automatically, it should be created according to a given rule in order to minimize the time required to accomplish the task.

Next, the user is asked if monitor measurement should be executed (ST 16). If the answer is "yes", monitor measurement commences (ST 17); if it is "no", the device proceeds to other processing (ST 18). When monitor measurement begins, measurement data are obtained which are based on physiological status transmitted from sensor probe 20. These monitor measurement data are displayed as numerical values or as a graph (or both) on display 3 (ST 19). The subject observes the data which are displayed and is thus able to determine whether his state is stable and to choose an appropriate time to begin recording the data. If, for example, the subject verifies that the measurement data being monitored are invariant, he can conclude that he has assumed a stable state.

When the monitor measurement data have been displayed, the user is asked if he wishes to terminate monitor measurement (ST 20). If he does, he uses keys 4 to select "terminate monitor measurement" (ST 21). If he does not, he is asked if he wishes to begin recording the measurement data (ST 22). If he replies "no" to this, the device returns to ST 19, displaying the monitor measurement data. If he replies "yes", he uses keys 4 to input the command to begin recording the measurement data (ST 23), and the mode is switched from monitor measurement to actual measurement. To simplify the operation, subject M need not be consulted in the aforesaid steps 20 and 22, but the data acquisition device itself can detect a key input to perform the operations which terminate monitor measurement or initiate actual measurement, thus going directly to steps 21 or 22. If these selections are not made, the device returns to ST 19.

When the command is given to begin recording the data, the measurement data, which are based on physiological data collected by the sensor probe just as in monitor measurement mode, are recorded (ST 24). The measurement data are stored in the file which name was determined in the aforesaid step 15. When data are being recorded, the measurement operation is executed according to the parameters (such as period of measurement and sampling interval) established earlier in device 1. Alternatively, if IC card 2 is used, the operation can follow the parameters established earlier on card 2. When a number of data sets must be managed in the same data memory space (e.g., when performing administrative tasks concerning files), the file names (identification names) established previously for the files and the measurement data can be stored in a way which preserves their relationship.

Next, the subject performs the exercise in a sequence which he determines himself (ST 25). While he exercises, the measurement data are stored under the file name which was selected. The data acquisition device 1 ascertains whether the key to terminate measurement has been depressed (ST 26). If it has, measurement is terminated (ST 28); if it has not, the device judges whether the measurement period established as a parameter has elapsed (ST 27). If it has, the device proceeds to ST 28, in which measurement is terminated, and it returns to ST 13, again displaying the main menu. If the measurement period has not yet elapsed, the device returns to ST 26.

With devices of the prior art, which lacked a monitor measurement mode, the only choice was to go directly from selecting an item on the menu in ST 14 or ST15 above to indicating that recording should begin in ST 23. If measurement is unsuccessful, it had to be terminated, and operation of IC card 2 had to be selected from the main menu in ST 14. The data recorded on IC card 2 then had to be erased, and the device would return to ST 23.

Figure 6:
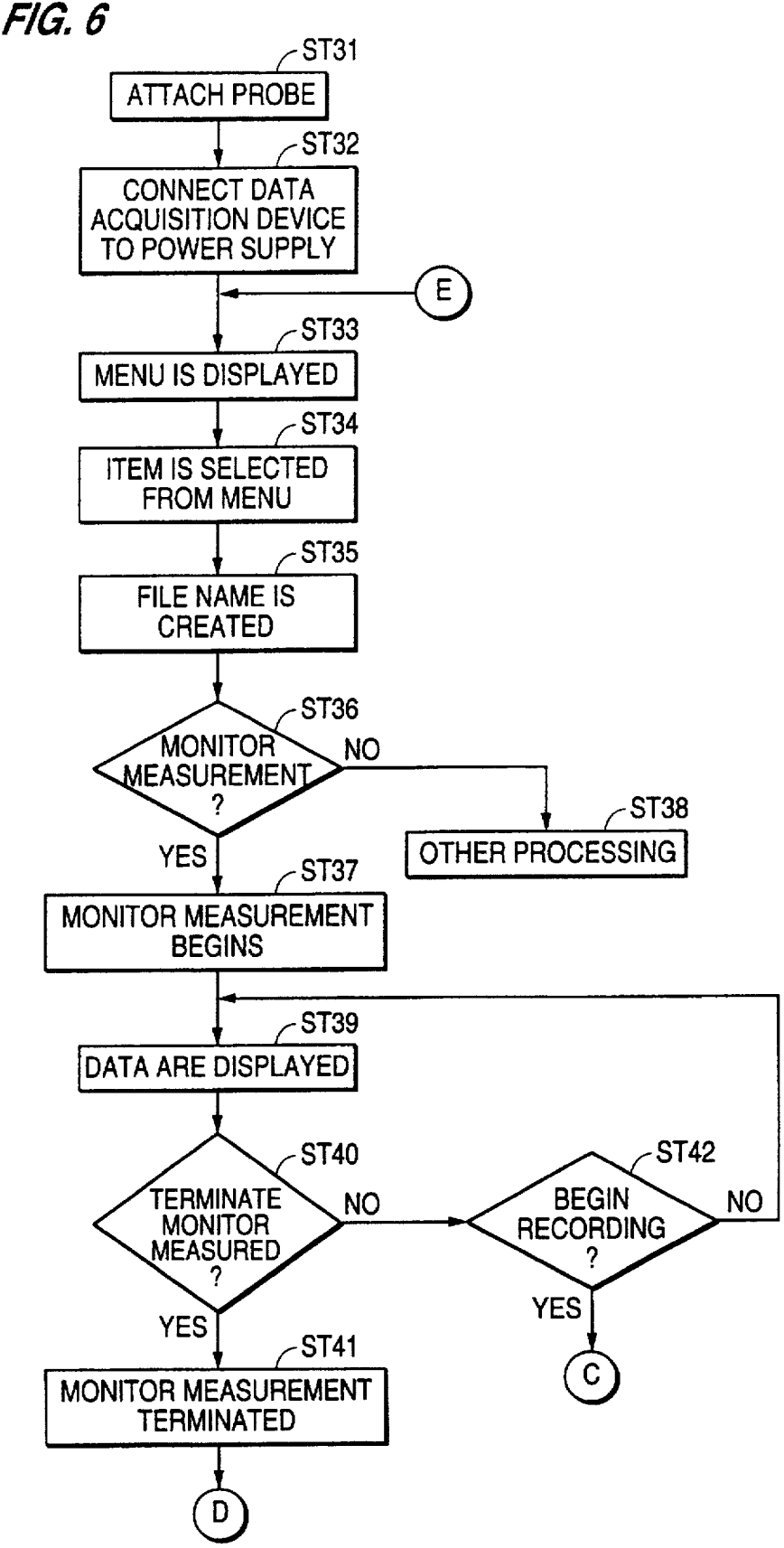
FIGS. 6 and 7 are flowcharts illustrating the operation of a second embodiment of the device of FIG. 1.
Figure 7:
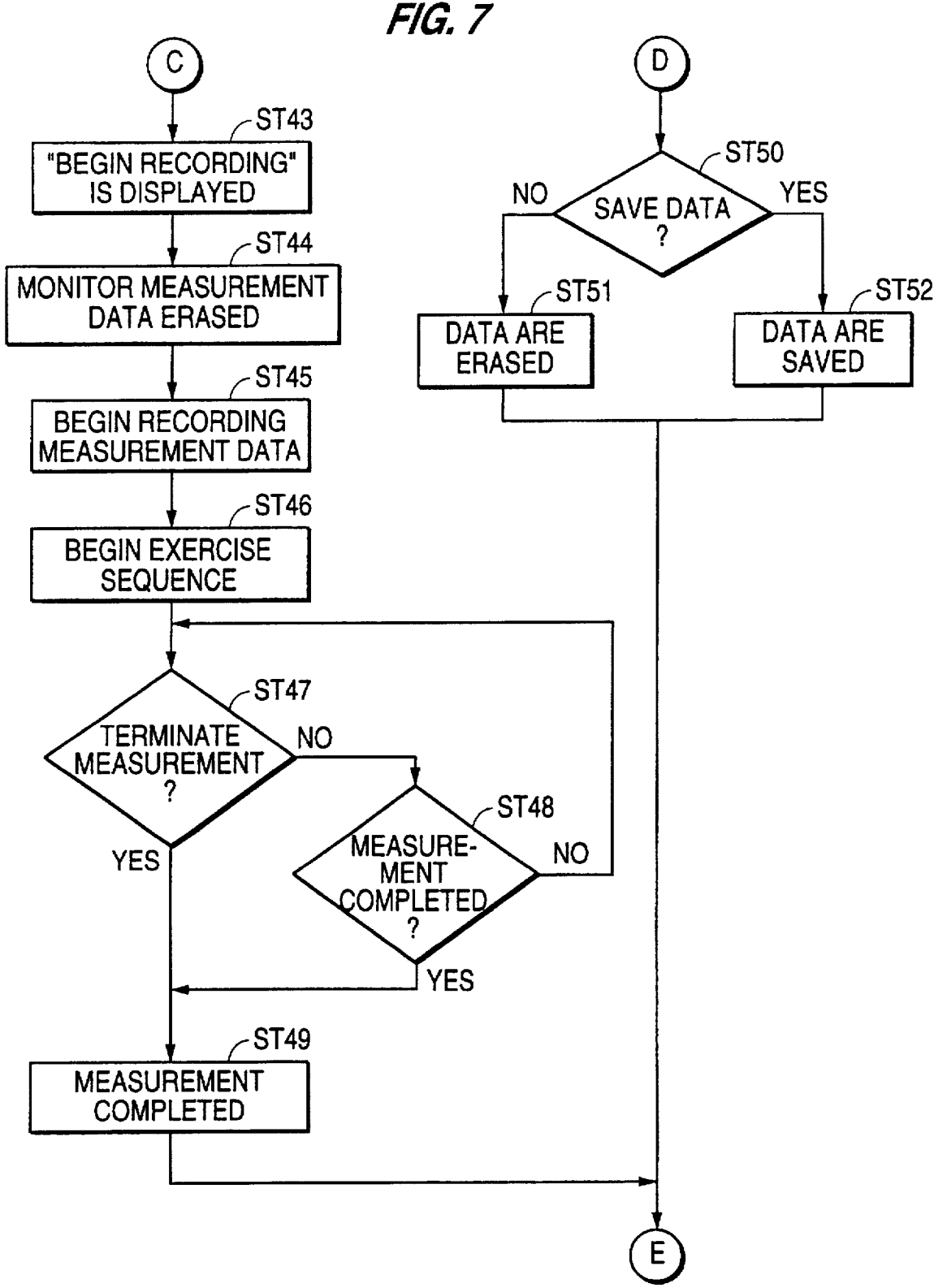

We shall now explain the operation (in monitor measurement mode) of the data acquisition device described in the second embodiment of this application, with reference to the flowchart in FIGS. 6 and 7. Since the basic flow of operations is identical to that shown in FIGS. 4 and 5, we shall discuss only the points where the two flowcharts differ.

In concurrent measurement mode (monitor measurement mode), the measurement data are stored temporarily in a specified file. When the user commands in step 42 that recording of the measurement data (i.e., actual measurement mode) should begin, the data recorded during monitor measurement are erased (ST 44). If "terminate monitor measurement" is selected in ST 40 and concurrent monitor measurement is terminated (ST 41), the user is asked whether the data recorded during concurrent monitor measurement should be saved (ST 50). If he answers "no", the measurement data in the file will be erased (ST 51); if he answers "yes", the data will be saved (ST 52).

In this version of the device, measurement data are recorded during monitor as well as actual measurement. Thus, even if the user forgets to command that data recording should begin before beginning his exercise sequence, he can prevent the data from being lost by selecting that they should be saved in a file when monitor measurement is completed.

As has been explained herein, the data acquisition devices described in embodiment 1 and 2 of this application can both perform monitor measurement, which allows the physiological state of the subject to be verified easily. Because the subject's state can be checked, the measurement never needs to be performed more than once. The device described in the second embodiment of this application stores the measurement data temporarily and concurrently during monitor measurement. If the user forgets to command that the data should be recorded during monitor measurement, he can still save them if needed by the selecting means, the device, then, prevents the loss of the measurement data.

Monitor measurement can be used to verify that the sensor is attached properly and that the data are not being affected by stray light so that the measurement never has to be redone because of those problems.

With these devices, the user can easily check his own state, and he can verify that the sensor is attached properly and that stray light is not affecting the measurements. These improvements allow the operational procedure required for measurement to be shortened, and they allow the memory capacity required for storage of measurement data to be reduced.

What is claimed is:

1. A data acquisition device, comprising:
  a receiver operable to receive a stream of data,
  a first input device operable to supply an identifier to identify data from the stream of data received by the receiver,
  a second input device operable to produce a signal indicative of whether data from the stream of data received by the receiver is valid,
  storage operable to store the identifier supplied by said first input device in combination with data from the stream of data received by the receiver, and
  a controller operable to operate the device in a monitor mode in which data from the stream of data received by the receiver is monitored and a measurement mode in which data from the stream of data received by the receiver is stored in said storage along with the identifier supplied by said first input device, wherein the controller is operable to switch operation of said device from said monitor mode to said measurement mode when the signal produced by said second input device indicates that the data is valid.

2. The data acquisition device of claim 1, further comprising a display operable to display measurements based on the data from the stream of data received by the receiver.

3. The data acquisition device of claim 2, wherein said device is operable to display the measurements without storing the data from the stream of data in the storage when said device is operating in the monitor mode.

4. The data acquisition device of claim 1, wherein the stream of data received by the receiver is produced by a sensor that detects physiological data while a person is exercising.

5. The data acquisition device of claim 1, wherein the device is operable in a concurrent monitor/measurement mode in which the device temporarily stores data from the stream of data received by the receiver in said storage, and wherein the controller is operable to switch operation of said device from said concurrent monitor/measurement mode to said measurement mode when the signal produced by said second input device indicates that the data is valid.

6. The data acquisition device of claim 5, further comprising a display operable to display measurements based on the data from the stream of data received by the receiver.

7. The data acquisition device of claim 5, further comprising means for producing a signal indicative of whether to abandon or save the data temporarily stored in said storage, wherein said controller is operable to erase the temporarily stored data from the storage when the signal indicates that the data should be abandoned and to save the temporarily stored date when the signal indicates that the data should be saved.

8. The data acquisition device of claim 7, wherein said controller is operable to erase or save the temporarily stored data when the controller switches operation of said device from said concurrent monitor/measurement mode to said measurement mode.

9. The data acquisition device of claim 5, wherein the stream of data received by the receiver is produced by a sensor that detects physiological data while a person is exercising.

10. A data acquisition device of claim 1, wherein said storage is an IC card.

* * * * *